United States Patent
Stites et al.

(10) Patent No.: US 7,919,070 B2
(45) Date of Patent: Apr. 5, 2011

(54) MULTI-ZONE REFORMING METHODS AND APPARATUS FOR CONVERSION OF DEVOLATILIZED BIOMASS TO SYNGAS

(75) Inventors: Ronald C. Stites, Brighton, CO (US);
Kevin T. Biehle, Broomfield, CO (US);
Robert E. Klepper, Arvada, CO (US);
Richard Ridley, Loveland, CO (US)

(73) Assignee: Range Fuels, Inc., Broomfield, CO (US)

( * ) Notice: Subject to any disclaimer, the term of this patent is extended or adjusted under 35 U.S.C. 154(b) by 0 days.

(21) Appl. No.: 12/628,409

(22) Filed: Dec. 1, 2009

(65) Prior Publication Data
US 2010/0137459 A1    Jun. 3, 2010

Related U.S. Application Data

(60) Provisional application No. 61/119,062, filed on Dec. 2, 2008.

(51) Int. Cl.
*C01B 3/26* (2006.01)
*C01B 3/24* (2006.01)
*C01B 31/18* (2006.01)
*C07C 1/02* (2006.01)

(52) U.S. Cl. ............. 423/651; 423/418.2; 423/650; 252/373

(58) Field of Classification Search ......... 423/418.2, 423/650, 651; 252/373
See application file for complete search history.

(56) References Cited

U.S. PATENT DOCUMENTS
6,863,878 B2   3/2005   Klepper

FOREIGN PATENT DOCUMENTS
| JP | 59-054602 A | 3/1984 |
| JP | 2003-336079 A | 11/2003 |
| JP | 2007-023084 A | 2/2007 |

OTHER PUBLICATIONS

Mudge et al., catalytic destruction of tars in biomass-derived gas, (Res. Thermochem. Biomass conversion, international conference (1988), 1141-1155.*
Computer transtion of JP 2007023084 (2007).*

* cited by examiner

*Primary Examiner* — Jafar Parsa
(74) *Attorney, Agent, or Firm* — O'Connor & Company; Ryan P. O'Connor

(57) ABSTRACT

The present invention provides improved methods and apparatus for producing syngas from any carbon-containing feed material. In one aspect, a multi-zone reformer system is provided. A first reaction zone can reduce the presence of refractory tars, while a second reaction zone in communication with the first reaction zone can steam-reform methane and other components from the first reaction zone, to generate high-quality syngas suitable for conversion to liquid fuels, such as ethanol. Other embodiments employ a plurality of reaction zones for added system functionality.

9 Claims, 2 Drawing Sheets

US 7,919,070 B2

MULTI-ZONE REFORMING METHODS AND APPARATUS FOR CONVERSION OF DEVOLATILIZED BIOMASS TO SYNGAS

PRIORITY DATA

This patent application claims priority under 35 U.S.C. §120 from U.S. Provisional Patent Application No. 61/119,062 for "MULTI-ZONE REFORMING METHODS AND APPARATUS FOR CONVERSION OF DEVOLATILIZED BIOMASS TO SYNGAS," filed Dec. 2, 2008, the disclosure of which is hereby incorporated by reference herein for all purposes.

FIELD OF THE INVENTION

The present invention generally relates to processes for the conversion of carbonaceous feedstocks, such as cellulosic biomass, into synthesis gas.

BACKGROUND OF THE INVENTION

Synthesis gas, which is also known as syngas, is a mixture of gases comprising carbon monoxide (CO) and hydrogen ($H_2$). Generally, syngas may be produced from any carbonaceous material. In particular, biomass such as agricultural wastes, forest products, grasses, and other cellulosic material may be converted to syngas.

Syngas is a platform intermediate in the chemical and biorefining industries and has a vast number of uses. Syngas can be converted into alkanes, olefins, oxygenates, and alcohols such as ethanol. These chemicals can be blended into, or used directly as, diesel fuel, gasoline, and other liquid fuels. Syngas can also be directly combusted to produce heat and power. The substitution of alcohols in place of petroleum-based fuels and fuel additives can be particularly environmentally friendly when the alcohols are produced from feed materials other than fossil fuels.

Problems associated with prior methods and apparatus for syngas production by devolatilization plus steam reforming include excessive methane or carbon dioxide production, as well as production of tars and aromatics. Other known limitations in these systems include high costs of materials of construction, and mechanical problems caused by thermal stresses at high temperatures.

In view of the aforementioned problems and limitations in the art, improved methods and systems are needed to produce syngas from biomass.

SUMMARY OF THE INVENTION

In one aspect of the present invention, a reformer system is provided, comprising:
(a) an input stream(s) to the reformer system;
(b) a first zone capable of reducing the molecular weight of refractory tars, if present in the input stream(s), wherein the first zone has a first output stream;
(c) a second zone capable of steam reforming of methane, if present in the input stream(s) or in the first output stream, wherein the second zone has a second output stream;
wherein the input stream(s) is in communication with the first zone, and
wherein the first zone is in communication with the second zone.

In some embodiments, the first zone is capable of substantial destruction of any refractory tars present in the input stream(s). In some embodiments, the temperature of the first zone is at least 1700° F., at least 1800° F., or between about 1850-1900° F. In some embodiments, the first zone is capable of destruction of at least a portion of BTEX species (i.e., benzene, toluene, ethylbenzene, and xylenes) present in the input stream(s).

In some embodiments, the temperature of the second zone is at least 1900° F., at least 2000° F., or between about 2000-2100° F. The second zone, in some embodiments, is capable of steam reforming of at least a portion of BTEX species present in the first output stream. These BTEX species can include BTEX species present in the input stream(s), or BTEX species produced in the first zone.

Optionally, the first zone can include a catalyst suitable for reducing the molecular weight of refractory tars. Optionally, the second zone can include a steam-reforming catalyst.

In some embodiments, the reformer system further comprises (d) a third zone capable of cooling the second output stream. Preferably, the temperature of the third zone is lower than the temperature of the first zone and/or lower than the temperature of the second zone. In some embodiments, the temperature of the third zone is selected from about 1000-1600° F., such as about 1300-1500° F.

The third zone can include means for removing solid and/or liquid species present in the second output stream, such as a filter, cyclone, or other separation device.

Another aspect of the invention relates to methods for reforming carbon-containing materials to produce syngas. In this aspect, the method comprises:
(a) combining a carbon-containing feedstock, including refractory tars, with steam, thereby generating an input stream;
(b) introducing the input stream into a first reaction zone under conditions effective to reduce the molecular weight of the refractory tars, thereby generating a first output stream including methane; and
(c) introducing the first output stream into a second reaction zone under conditions effective to steam reform at least some of the methane, thereby generating a second output stream including syngas.

In some embodiments, during step (b), the refractory tars are substantially destroyed. The temperature of the first zone can be at least 1700° F., at least 1800° F., or between about 1850-1900° F. The residence time of the first zone can be selected from about 0.1-10 seconds.

In some methods, BTEX species are present in the input stream. During step (b), the average molecular weight of at least a portion of the BTEX species is preferably reduced. In some embodiments, the temperature of the second zone is at least 1900° F., at least 2000° F., or between about 2000-2100° F. In some embodiments, the residence time of the second zone is selected from about 1 millisecond to about 10 seconds.

In some methods, BTEX species are present in the first output stream. During step (c), at least a portion of the BTEX species is preferably steam reformed, i.e. converted into syngas. These BTEX species can include BTEX species present in the input stream, BTEX species produced in the first reaction zone, or some other source.

Certain embodiments employ catalyzed reduction of the molecular weight of refractory tars within the first reaction zone. Certain embodiments include catalyzed steam reforming within the second reaction zone. The reactor walls of either reaction zone can include an active catalyst, such as Ni.

Some method embodiments further include (d) introducing the second output stream into a third zone under conditions effective for cooling the second output stream. The temperature of the third zone is preferably lower than the temperature of the first zone and/or second zone. In some embodiments, the temperature of the third zone is selected from about 1000-1600° F., such as about 1300-1500° F. This step (d) can also include removing at least some solid and/or liquid species (such as species that did not reform into syngas).

In some methods, the carbon-containing feedstock is obtained from a devolatilization unit. For example, the carbon-containing feedstock can be devolatilized biomass.

In certain embodiments, the syngas produced is converted into one or more $C_1$-$C_4$ alcohols, such as ethanol.

Some variations of this invention provide a method of producing ethanol, the method comprising:
(a) devolatilizing biomass to produce devolatilized biomass and refractory tars;
(b) combining (i) the devolatilized biomass and refractory tars with (ii) steam, thereby generating a first stream;
(c) introducing the first stream into a first reaction zone under conditions effective to reduce the molecular weight of the refractory tars, thereby generating a second stream including methane;
(d) introducing the second stream into a second reaction zone under conditions effective to steam reform at least some of the methane, thereby generating a third including syngas; and
(e) converting at least a portion of the syngas to ethanol under suitable catalyzed reaction conditions.

Figure 1:
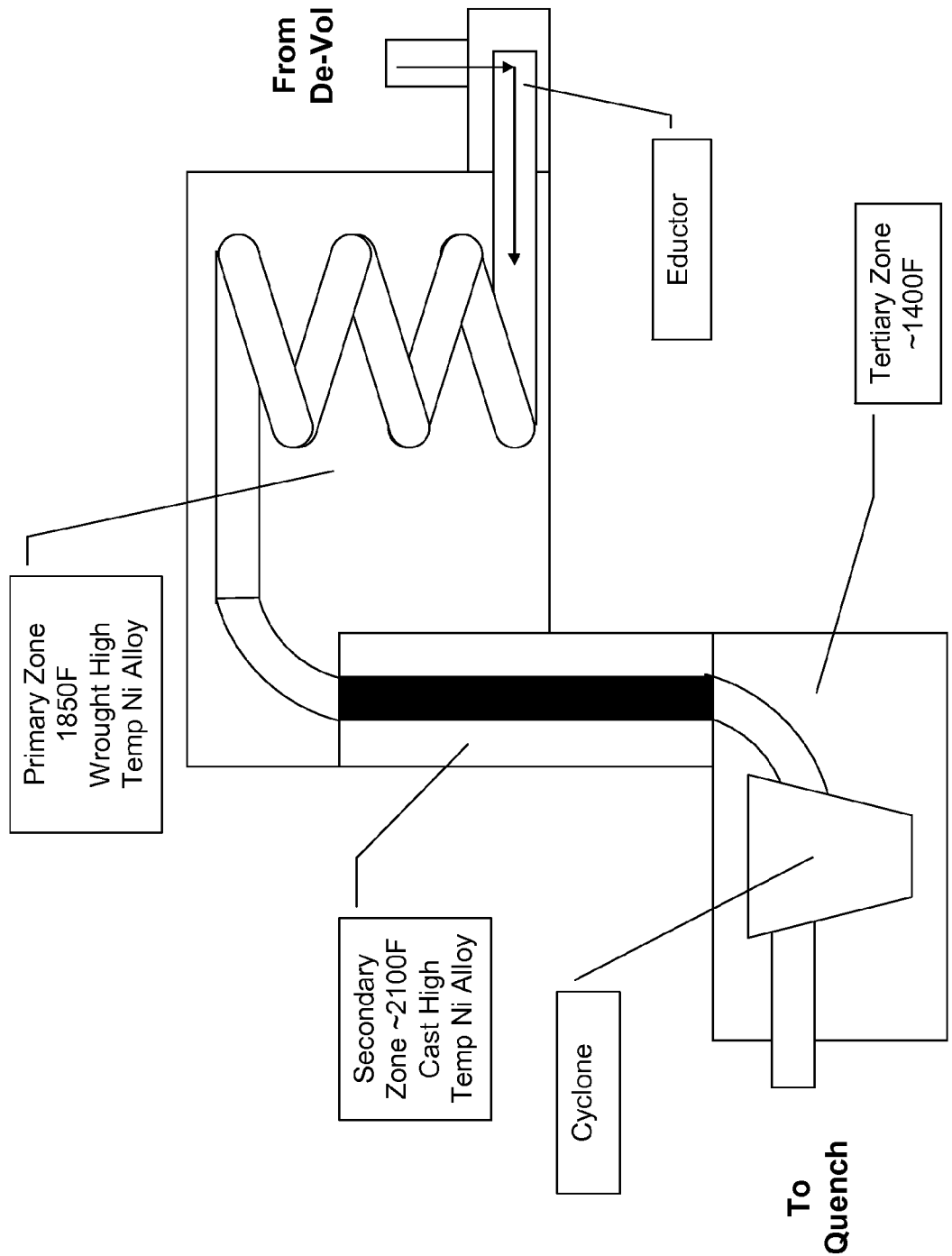
FIG. 1 is a simplified process-flow diagram depicting a reformer system, according to some embodiments of the invention.
Figure 2:
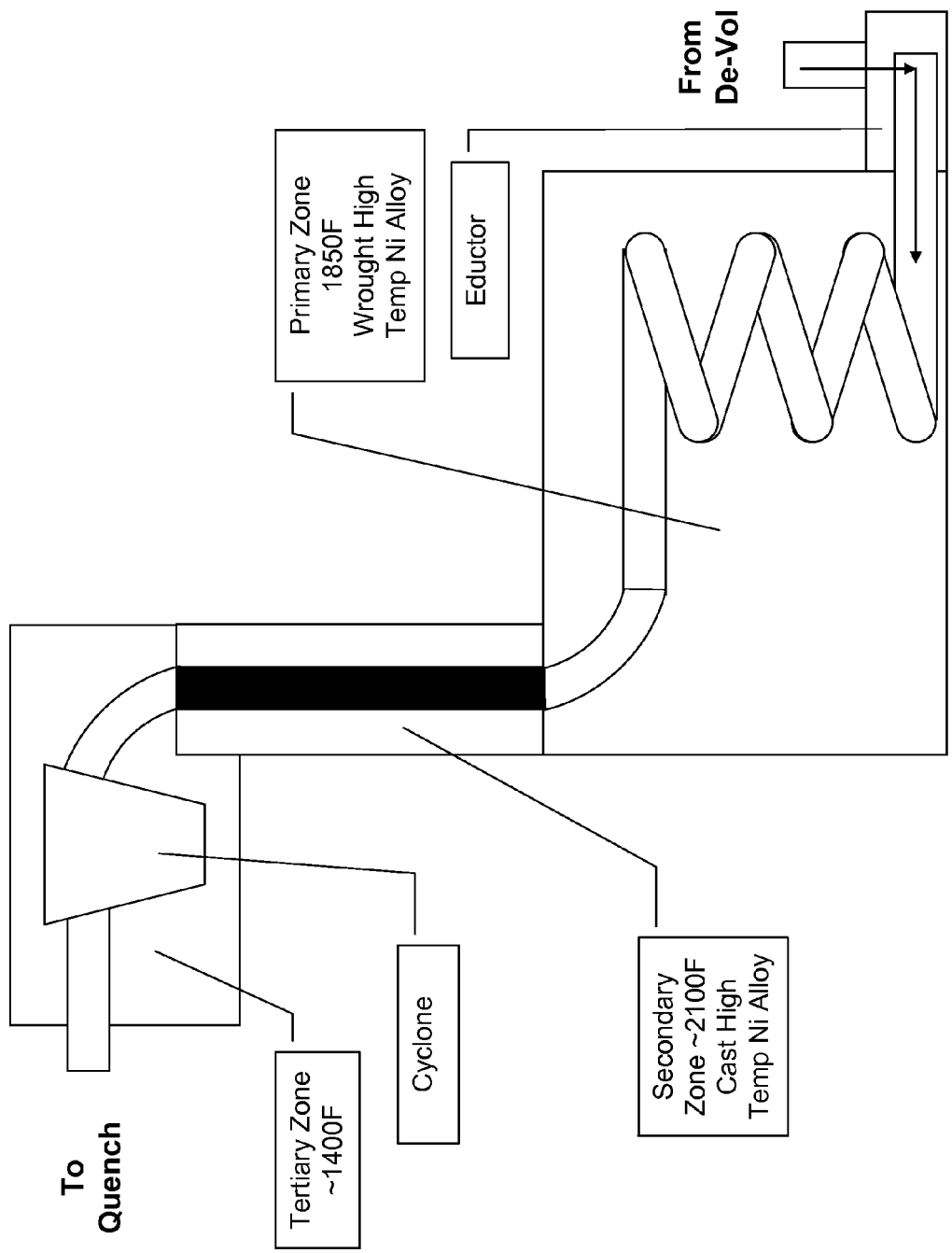
FIG. 2 is a simplified process-flow diagram depicting a reformer system, according to some embodiments of the invention.

These and other embodiments, features, and advantages of the present invention will become more apparent to those skilled in the art when taken with reference to the following detailed description of the invention in conjunction with the accompanying drawings.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

All publications, patents, and patent applications cited in this specification are incorporated herein by reference in their entirety as if each publication, patent, or patent application was specifically and individually put forth herein.

The following detailed description should be read with reference to the drawings, in which identical reference numbers refer to like elements throughout the different figures. The drawings, which are not necessarily to scale, depict selected embodiments and are not intended to limit the scope of the invention. The detailed description illustrates by way of example, not by way of limitation, the principles of the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. If a definition set forth in this section is contrary to or otherwise inconsistent with a definition set forth in patents, published patent applications, and other publications that are herein incorporated by reference, the definition set forth in this specification prevails over the definition that is incorporated herein by reference.

The present invention provides methods and apparatus for producing syngas from any carbon-containing feed material. The present invention relates to improved systems that include biomass devolatilization and steam reforming to produce syngas, and improved methods to operate such systems.

The methods and systems of the invention can accommodate a wide range of feedstocks of various types, sizes, and moisture contents. Any carbon-containing compound can be used as a feed material for the production of syngas. For example, biomass such as agricultural wastes, forest products, grasses, and other cellulosic material can be used. In some embodiments, the feedstock includes one or more materials selected from timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth.

In some variations, biomass or another carbon-containing feed material is introduced into a devolatilization unit such as that described in U.S. Pat. No. 6,863,878 or in U.S. patent application Ser. No. 12/166,167 (filed Jul. 1, 2008). The product that exits the devolatilization unit can include a gas phase and a solid phase and can (in some embodiments) further include one or more liquid phases. It is preferred to produce a solid phase and a gas phase from the devolatilization unit.

Devolatilization can be conducted at a variety of temperatures, such as temperatures between about 900° F. and 1500° F., preferably about 1200-1400° F. Devolatilization can be conducted at a variety of residence times of the solid and gas phases. For example, solid residence times can be about 1 minute to about 30 minutes, such as about 5-10 minutes. Gas residence times can be about 100 milliseconds to about 10 seconds, such as about 1-5 seconds.

The gas phase from the devolatilization unit preferably includes syngas, and will typically also include methane and carbon dioxide. A stream exiting the devolatilization unit is introduced, along with steam (either already present or then added) into a reformer system, where syngas is produced from both devolatilized solids as well as from methane produced during devolatilization. The steam-reforming reaction of methane is $$CH_4 + H_2O \rightarrow CO + 3H_2$$

The reaction stoichiometry for steam reforming of solid material will depend on the specific composition of species that are converted.

The gas phase from the devolatilization unit can include aromatic compounds such as benzene, toluene, ethylbenzene, and xylenes (collectively known as "BTEX"). Furthermore, the gas phase from the devolatilization unit can include heavier aromatic compounds, such as refractory tars. For purposes of the present disclosure, "refractory tars" are chemical species having a molecular weight greater than about 100 g/mol, and do not include BTEX species.

In some embodiments of the invention, the reformer system includes a first zone effective for reduction of molecular weight of refractory tars present in the input stream to the reformer system. In preferred embodiments, the first zone is effective for substantial destruction of any refractory tars present. By "substantial destruction," it is meant that the average molecular weight of refractory tars is reduced to about 100 g/mol or less.

Conditions for this first zone can be adjusted and optimized. For example, the temperature for this first zone can be selected from about 1700° F. or greater, preferably about 1800° F. or greater, and more preferably about 1850-1900° F. The upper temperature is practically limited by economic and safety considerations with respect to materials of construction. The residence time for the first zone can be selected from about 0.1-10 seconds, such as about 1 second.

Substantial destruction of refractory tars can produce BTEX components. In certain embodiments, the first zone is also effective for destruction of at least a portion of BTEX species, such as conversion to carbon oxides and/or light hydrocarbons.

In some embodiments, the reformer system includes a second zone effective for steam reforming of methane. The temperature for this second zone can be selected from about 1900° F. or greater, preferably about 2000° F. or greater, and more preferably about 2000-2100° F., for example. The upper temperature is practically limited by economic and safety considerations with respect to materials of construction. The residence time for the second zone can be selected from about 1 millisecond to about 10 seconds, such as (for example) about 100-500 milliseconds.

In some embodiments, conditions for the second zone are selected to be effective for steam reforming of BTEX components present. These BTEX components can be those produced during devolatilization or can be BTEX derived from refractory tars in the first zone, or both of these. Additionally, in some embodiments, conditions for the second zone are selected to be effective for steam reforming of light hydrocarbons (e.g., ethane, ethylene, propane, etc.) derived from refractory tars in the first zone.

In some embodiments, the reformer system includes a third zone effective for cooling the process stream. Conditions for this third zone can vary but the temperature should be lower than the temperature of either the first zone or second zone. For example, the temperature for this third zone can be selected from about 1000-1600° F., preferably about 1300-1500° F., and more preferably about 1350-1450° F. The residence time for the third zone is not regarded as critical and can be selected from about 1-10 seconds or some other amount of time.

Cooling in the third zone is preferred, in some embodiments, in order to reduce thermal loads on downstream operations and reduce thermal stress on components contained in the third zone. Such components in the third zone can include, for example, a cyclone or other means of solid/gas (or liquid/gas) separation, suitable for removing solid or liquid materials that do not reform in the prior zones. These solid or liquid materials can include ash, metals, char, and particularly unreactive refractory tars and polymeric species.

Preferred embodiments of the invention employ a multizone reforming furnace. The invention is not so limited, however. The reformer system apparatus can include any reactor (or plurality of reactors) suitable for including the three or more zones as described herein. Conventional steam reformers, well-known in the art, can be used. Other options include autothermal reformers, partial-oxidation reactors, and reactors that combine several reaction mechanisms (e.g., partial oxidation followed by water-gas shift). The reactor configuration can include zones employing a fixed bed, a fluidized bed, a plurality of microchannels, or some other configuration.

Materials of construction should be selected to provide an economical, practical, and safe apparatus. In some embodiments, the first zone includes a wrought high-temperature nickel-based alloy. In some embodiments, the second zone includes a cast high-temperature nickel-based alloy. Specific selection of nickel-based alloys is well within the skill of an ordinary artisan.

The second zone, in preferred embodiments, can be configured with a pipe or other simple geometry using cast materials. Such a configuration offers the advantages of reduced thermal stress (and possible failure), as well as more-convenient replacement of components.

In various embodiments, one or more of the zones in the reformer system includes a catalyst suitable for steam reforming of methane, light hydrocarbons, BTEX, and/or refractory tars. Catalysts can be present in a variety of forms, including pellets, spheres, and powder. Catalysts can be supported or unsupported.

Some embodiments employ substantially homogeneous (non-catalyzed) chemistry in one or more zones. If desired, chemistry at reactor walls can be minimized by appropriate selection of materials that tend to be more inert under process conditions, or by selecting a relatively large reactor diameter.

In some embodiments of the invention, reactor zones do not include a distinct catalyst phase, but the reactor walls comprise an active catalyst, such as (but not limited to) nickel. In some embodiments, minerals derived from the feed material are catalytically active for steam reforming. Such minerals may include iron, potassium, aluminum, magnesium, and calcium, for example. Catalysis caused by feedstock-derived minerals could occur anywhere and would not be limited to reaction at walls of the reactor.

Some variations of the invention include first and second zones as described, but do not include cooling or solid/gas separation. Some variations of the invention do not include a devolatilization step or unit prior to the reformer system.

Other variations of the invention include additional zones. Generally, the invention features a reformer system having multiple zones, which means two or more zones. Multiple zones can be contained within a single physical reactor. Alternatively, multiple zones can be accomplished by a plurality of physically separate reactors. Delineation of zones is not tied to physical equipment (e.g., inlets, outlets, eductors, or valves), but rather to process functionality in accordance with the description of zones herein.

In some embodiments, three zones are utilized. In various embodiments, four, five, or more zones are employed within the reformer system. When additional zones are employed, the additional zones can be designed to have similar conditions and functionality as one of the other zones. Alternately, additional zones having other conditions and functionality can be included within an overall reformer system. Heat integration can be included across some or all of the zones present.

In certain embodiments of the invention, process performance within a zone can be used to tune conditions for that zone or for any other zone, according to various process-control strategies. For example, a sample could be taken from the second zone to measure the BTEX concentration. Based on that analysis, the temperature in the first zone could be adjusted. Or, methane concentration in the first zone could be used to adjust residence time in the second zone, and so forth. This type of control could be conducted dynamically or using certain time-based averages, as will be appreciated.

Certain preferred embodiments of the present invention allow for reduced $CH_4$ content, reduced $CO_2$ content, and reduced BTEX content—i.e. better syngas quality and/or yield—compared to a single-zone process. Enhanced syngas quality will typically be a benefit for downstream operations utilizing the syngas. Some preferred embodiments will also minimize thermal stresses, reduce materials costs, and minimize downtime associated with the reformer system.

In some variations, the syngas from the reformer system is filtered, purified, or otherwise conditioned prior to being converted to another product. For example, the cooled and compressed syngas may be introduced to a syngas conditioning section, where BTEX, sulfur compounds, nitrogen, metals, and/or other impurities are optionally removed from the syngas.

The syngas produced as described according to the present invention can be utilized in a number of ways. Syngas can generally be chemically converted and/or purified into hydrogen, carbon monoxide, methane, graphite, olefins (such as ethylene), oxygenates (such as dimethyl ether), alcohols (such as methanol and ethanol), paraffins, and other hydrocarbons. The syngas produced according to the methods and systems of the invention can further produce a linear or branched hydrocarbon, diesel fuel, gasoline, waxes, or olefins by Fischer-Tropsch chemistry; methanol, ethanol, and mixed alcohols by a variety of catalysts; isobutane by isosynthesis; ammonia by hydrogen production followed by the Haber process; aldehydes and alcohols by oxosynthesis; and many derivatives of methanol including dimethyl ether, acetic acid, ethylene, propylene, and formaldehyde by various processes.

In certain embodiments, the syngas is converted to high yields of alcohols, particularly ethanol. Syngas can be selectively converted to ethanol by means of a chemical catalyst, such as described in U.S. patent application Ser. No. 12/166,203, entitled "METHODS AND APPARATUS FOR PRODUCING ALCOHOLS FROM SYNGAS," filed Jul. 1, 2008, whose assignee is the same as the assignee of this patent application, and which is hereby incorporated herein by reference.

The syngas produced according to the methods and systems of the invention can also be converted to energy. Syngas-based energy-conversion devices include a solid-oxide fuel cell, Stirling engine, micro-turbine, internal combustion engine, thermo-electric generator, scroll expander, gas burner, thermo-photovoltaic device, or gas-to-liquid device. In some cases, the output syngas of two, or more, reactors can be combined to supply syngas to downstream subsystems comprised of syngas coolers, syngas cleaners, and syngas-based energy-conversion devices.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent that there are variations of the invention, which are within the spirit of the disclosure or equivalent to the inventions found in the appended claims, it is the intent that this patent will cover those variations as well. The present invention shall only be limited by what is claimed.

What is claimed is:

1. A method of producing syngas, said method comprising:
   (a) combining a carbon-containing feedstock, including refractory tars, with steam, thereby generating an input stream;
   (b) introducing said input stream into a first reaction zone under conditions effective to reduce the molecular weight of said refractory tars to an average molecular weight of 100 g/mol or less, thereby generating a first output stream including methane, wherein a temperature within said first reaction zone is at least 1700° F.;
   (c) introducing said first output stream into a second reaction zone under conditions effective to steam reform at least some of said methane, thereby generating a second output stream including syngas, wherein a temperature within said second reaction zone is at least 1900° F.; and
   (d) introducing said second output stream into a separation zone to remove at least some solid or liquid species present in said second output stream, wherein a temperature within said separation zone is less than 1600° F.

2. The method of claim 1, wherein during step (b), said refractory tars are substantially destroyed and then, during step (c), at least partially converted to syngas.

3. The method of claim 1, wherein BTEX species are present in said input stream, and wherein during step (b), the average molecular weight of at least a portion of said BTEX species is reduced.

4. The method of claim 1, wherein BTEX species are present in said first output stream, and wherein during step (c), at least a portion of said BTEX species is converted into syngas.

5. The method of claim 1, wherein said first reaction zone includes catalyzed reduction of the molecular weight of refractory tars.

6. The method of claim 1, wherein said second reaction zone includes catalyzed steam reforming.

7. The method of claim 1, wherein said separation zone is effective for cooling said second output stream.

8. The method of claim 1, wherein said carbon-containing feedstock is obtained from a devolatilization unit.

9. The method of claim 1, wherein said carbon-containing feedstock is devolatilized biomass.

* * * * *